United States Patent [19]

Shabalin et al.

[11] Patent Number: 5,561,067

[45] Date of Patent: Oct. 1, 1996

[54] METHOD OF DETERMINING THE SEVERITY OF A LITHOGENESIS CONDITION AND A COMPOSITION OF CALCULI FORMING SALTS

[76] Inventors: Vladimir N. Shabalin, ulitsa B. Galushkina, 3, korpus 1, kv. 21; Svetlana N. Shatokhina, prospekt Mira, 70, kv. 76, both of Moscow, Russian Federation

[21] Appl. No.: 341,531

[22] PCT Filed: May 6, 1993

[86] PCT No.: PCT/RU93/00105

§ 371 Date: Nov. 17, 1994

§ 102(e) Date: Nov. 17, 1994

[87] PCT Pub. No.: WO93/23753

PCT Pub. Date: Nov. 25, 1993

[30] Foreign Application Priority Data

May 21, 1992 [RU] Russian Federation .......... 5059948/14
Jun. 30, 1992 [RU] Russian Federation .......... 5065432/14

[51] Int. Cl.$^6$ .................................................. G01N 33/493
[52] U.S. Cl. ................. 436/74; 436/63; 436/73; 436/79; 436/99; 436/174; 436/181
[58] Field of Search .................................... 436/63, 73, 74, 436/79, 88, 99, 174, 181

[56] References Cited

U.S. PATENT DOCUMENTS

| 2,862,796 | 12/1958 | Gomberg | 436/86 |
| 4,877,206 | 7/1989 | Heinz | 436/63 |
| 5,366,899 | 11/1994 | Shabalin et al. | 436/88 |

FOREIGN PATENT DOCUMENTS

| 0252762 | 1/1988 | European Pat. Off. . |
| 0292311 | 11/1988 | European Pat. Off. . |
| 3643263 | 7/1988 | Germany . |
| 1573425 | 6/1990 | U.S.S.R. . |
| 1629846 | 2/1991 | U.S.S.R. . |
| 9202821 | 2/1992 | WIPO . |

OTHER PUBLICATIONS

X. Martin et al. *Kidney Int.* 1985, 28, 636–639.
K. A. Edyvane et al. *Clin. Chim. Acta* 1986, 157, 81–88.
E. M. Worcester et al. *Am. J. Physiol.* 1988, 255, F1197–F1205.
Predtechensky, V. E. *Manual for Clinical Laboratory Studies* Publishing House Medicine, 1964, pp. 420, 425–431, 445–446 (& an English translation of p. 427).
Predtechensky, V. E. *Manual for Clinical Laboratory Studies* Publishing House Medicine, 1964. pp. 452–454 (& an English translation thereof).
Schubert; Gernot, et al. "Crystalloptical and Microprobe . . . " *Z. Klin. Med.* 44 (1989), pp. 923–928. (& an English translation thereof).
Tiselius, H. G. "Measurement of the Risk of Calcium . . . " *Urological Research*, vol. 15, (1987) pp. 79–81.
Wandt, M. A. E., et al. "Covanance Biplot Analysis . . . " *British Journal of Urology*, vol. 61, (1988) pp. 474–481.
Nishino, Tadashi, et al. "An approach to dissolving kidney . . . " *Japanese Journal of Nephrology*, vol. 29, No. 5 (1987), pp. 571/73–575/77.

*Primary Examiner*—Arlen Soderquist
*Attorney, Agent, or Firm*—Ladas & Parry

[57] ABSTRACT

The present method for evaluating the extent of a lithogenesis process intensity and for determining the composition of lithogenic urate salts in urolithiasis resides in adding an aqueous protein solution to a urine sample in a ratio of 9:1, 7:1 or 5:1, respectively; applying the mixture thus-prepared as a drop onto a smooth surface for drying for at least 24 hours; determining the nature of crystallization of urate salts in the marginal zone of the urine sample, the presence of separate, singly occurring crystals, conglomerates of crystals and a complete crystallization of this marginal zone being indicative, respectively, of a weak, moderate or a highly pronounced extent of a lithogenesis process intensity; the composition of crystalline formations is determined, while, simultaneously, establishing the constitution of urate salts in the central zone of that same urine sample, followed by carrying out a comparative analysis to said two compositions to determine the composition of lithogenic urate salts.

18 Claims, No Drawings

METHOD OF DETERMINING THE SEVERITY OF A LITHOGENESIS CONDITION AND A COMPOSITION OF CALCULI FORMING SALTS

FIELD OF THE INVENTION

The present invention relates to analytical methods for use in medicine and, more specifically, to a method for evaluating the extent of a lithogenesis process intensity and for determining the composition of lithogenic urate salts in urolithiasis.

BACKGROUND OF THE INVENTION

The problems of investigating the dynamic aspects of a lithogenesis process in the human organism, of studying its intensity, of determining the salt composition in the course of a lithogenesis process are currently being researched. Knowledge in this field makes it possible to prevent the formation of urate calculi, to introduce timely corrections into the lithogenesis process, to prescribe and carry out individual therapeutic treatment for urolithiasis cases.

Known in the prior art are methods for predicting urolithiasis based upon detecting a lithogenesis process, such as, e.g. a prediction method based upon detection of urate salt crystals in freshly discharged urine or in urine analyzed Shortly after urination (Ref. V. Ye. Predtechensky "Guide for Clinical Laboratory Investigations", 1964 Medicina Publishers, pp. 420–446), or a method for predicting urolithiasis (SU, A, 1 629 846) based upon evaluation of the crystal-forming activity of urine by mixing solutions of calcium chloride, sodium oxalate and urine, followed by holding the resultant mixture and then counting the number of crystals formed.

However, the above-cited methods are aimed only at detecting a lithogenesis process, and they do not allow the determination to be made as to the extent of this process intensity.

Equally known in the prior art is a method for predicting urolithiasis, in which it is recommended to evaluate the extent of risk of calcium phosphate crystallization in urine by counting the number of crystals thus-formed and having a specific size using recommended mathematical procedures (refer, please, to the "Urological Research", No. 2, 15, 1987, Springer-Verlag, H.-G. Tiselius, "Measurement of the Risk of Calcium Phosphate Crystallization in Urine", pp. 79–81). The latter methods calls for sophisticated mathematical calculations, and its only purpose is to detect the fact of a lithogenesis process.

Also known in the prior art is a method for predicting of urolithiasis (PCT/SU 91/00140), by preparing a protein solution, e.g. albumin solution is added to a urine sample, the resultant mixture is subjected to drying and, if a 100%-crystallization of the urine sample takes place, a urolithiasis case is predicted. The latter method is also aimed at revealing a lithogenesis process, and it cannot be used for evaluating the extent of intensity of a lithogenesis process.

Moreover, there are known in the prior art methods for determining the composition of urate salts participating in urolithiasis (V. Ye. Predtechensky "Guide for Clinical Laboratory Investigations", 1964 Medicina Publishers, Moscow, pp. 452–454; Wandt M., Underhill L. "Brit. J. Urol.", 1988 61 No. 6 478–481; Schubert G., Brien G., Adam K. "Z. Klin. Med.", 1989, 44, No. 11 , 923–928; Nichino T., Sakura T., Sato T., Koiso K., Kaneko S. "Jap. J. Nephrol.", 1987, 29, No. 5, 571–575). All of the above-cited methods are based upon study of the urine constituents (salt deposit, sand, concretions) by the physico-chemical route using adsorption, ion exchange, such as, e.g. chromatography, using X-ray structural analysis, X-ray spectral analysis, thermal analysis involving study of nuclear magnetic resonance, electron para-magnetic resonance and other spin effects.

All of the above-cited methods are suitable only for study of already formed calculi discharged from the human body, and they unable to determine the chemical nature of nascent calculi at early urolithiasis stages, and that of calculi already fully formed, but not withdrawn from the body.

There exists in the prior art no method for determining the chemical composition of calculi-forming urate salts at early urolithiasis stages, or for determining that of calculi fully formed, but not discharged from the organism.

DESCRIPTION OF THE INVENTION

The proposed method for evaluating the extent of intensity of a lithogenesis process and for determining the composition of calculi-forming urates during urolithiasis is novel and has never been described in the literature.

The present invention is aimed at developing a method which would make it possible to evaluate —quickly and accurately—the extent of intensity of lithogenesis process during urolithiasis process, as well as to determine the salt composition of an urate calculus at any stage of its formation.

The above-formulated problem is solved owing to the following improvements introduced into the method for evaluating the intensity of a lithogenesis process and for determining the composition of lithogenic urate salts in urolithiasis: into a urine sample an aqueous protein solution is added in a ratio of 9:1, 7:1 or 5:1, respectively; the mixture thus-prepared is applied as a drop onto a smooth flat surface, followed by drying the drop for at least 24 hours; assessment is made of the nature of crystallization of urate salts in the marginal zone of the urine sample; if any individual crystals, crystalline conglomerates or in case of a complete crystallization of this marginal zone, judgement is made on a weak, moderate or a deeply pronounced extent of intensity of a lithogenesis process; the composition of these crystalline formations is determined, while, simultaneously, determining the composition of urate salts in the central zone of that same urine sample, followed by making a comparative analysis of these two compositions for detecting the presence of lithogenic urate salts.

It is preferable that, as said aqueous protein solution, use be made of an 8–12%-aqueous albumin solution. To improve the analysis accuracy,it is advisable that drying of a mixture drop applied onto a smooth surface be conducted at room temperature. In order to speed up and improve accuracy of the analysis, it is preferable that X-ray spectrum microanalysis be used for analyzing the elemental composition of said crystalline formations.

The method in accordance with the present invention has elicited the following fact: there exists a relationship between the intensity of the calculus formation process and the intensity of crystallization of urate salts in the marginal zone of a urine sample. This phenomenon makes it possible to rapidly and accurately determine in a urine sample the extent of the intensity of a lithogenesis process, thus providing a possibility to study the lithogenesis process in its dynamic aspects, to introduce timely corrections into this process thereby preventing the formation of a urate calculus, and—if need be—to work out and follow an individual therapeutic treatment course. Moreover, the method of the present invention makes it possible, well in advance of the actual fact of the formation of a calculus in the human body, to determine the composition of calculi-forming urate salts and to take adequate purposeful measures for removing these urate salts from the body and for preventing their intake together with potable water and food stuffs. The present analytical method makes it possible to learn, exactly what calculi-forming urate salts constitute the surface layer of a calculus during a certain period of observation, if a calculus is detected in the urinary ways of a patient, since this information may be required, e.g. for lithotripsy.

A study of the composition of lithogenic urate salts in a dynamic aspect (including from the very moment of the onset of a calculus formation process) makes it possible to establish the composition and subsequent structure of the entire calculus, which fact is important, if lithotripsy is envisaged.

Finally, the present method of analysis makes it possible to carry out effective prophylaxis against urolithiasis recidives. The present method is convenient, simple to carry out, and does not require any special equipment.

PREFERRED EMBODIMENT OF THE INVENTION

As stated above, the present method for evaluating the extent of intensity of a lithogenesis process is based upon the established relationship between the degree of salt crystallization in the marginal zone of a urine sample and the calculus formation intensity. The present method is carried out as follows:

Into a urine sample an aqueous protein solution (it is preferable that an 8–12%-aqueous albumin solution be used) is added in a ratio of 9:1, 7:1 or 5: 1, respectively. For the purpose of analysis, it is possible to use a urine sample taken in one of the above-specified ratios with the aqueous albumin solution. For the sake of authenticity of an analysis, it is possible to use two or three alternative ratios. One drop of a mixture thus—obtained is applied onto a flat surface, followed by drying for at least 24 hours at room temperature.

Once the drop is dried up, the intensity of urate salt crystallization is assessed in the marginal zone of the urine sample: the presence of separate single crystals is indicative of a weak intensity of the calculus formation process, the presence of conglomerates of salt crystals—of a moderate intensity, and a complete crystallization of this marginal zone is indicative of a deeply pronounced intensity of a calculus formation process.

The absence of crystals in the marginal zone testifies to the fact that no lithogenesis process takes place. The present method makes it possible to achieve a two-pronged purpose, namely: to evaluate the extent of the process intensity and, at the same time, to determine the composition of lithogenic urate salts. Physical analytical methods (preferably X-ray spectrum microanalysis) are used to determine the elemental constitution of crystalline formations found in the marginal zone. At the same time, the elemental constitution of urate salts in the central zone of that same urine sample is determined, whereupon a comparative analysis of these two constitutions is conducted, on the basis of which a conclusion is drawn on the chemical composition of calculus-forming urate salts. It should be borne in mind that a calculus formation process is a dynamic process, and, therefore, a salt constitution may vary in time. The present method makes it possible to determine the salt constitution of a calculus as it is formed or may be formed in the future with the given salt constitution of urine.

The method of the present invention has undergone tests in clinical laboratories. To evaluate the extent of the intensity of the lithogenesis process, 12 patients belonging to the category of the so-called "calculus dischargers" (i, e. patients, in whom spontaneous destruction and discharge of calculi is observed) and 128 practically healthy persons in their pre-clinical urolithiasis stage, have been examined. The fact that these practically healthy persons are in their pre-clinical urolithiasis stage has been established by the conventional method, but the extent of the intensity of the lithogenesis process remained unknown. The following investigation procedure has been used: a urine sample was taken, an aqueous protein (albumin) solution was added thereto in a ratio of 9:1, 7:1 or 5:1, respectively, the mixture thus-obtained was applied as a drop onto a microscopic slide, and dried at room temperature for 24 hours. Then, a study has been undertaken to find, whether there are any crystals in the marginal zone of the dried urine sample. The study results are reported in Tables 1 and 2 that follow:

TABLE 1

The results of clinical and laboratory tests on patients belonging to the category of "calculi dischargers"

| Nos. | Patients | Urine/aqueous albumin solution ratio | | | Extent of lithogenesis process |
|---|---|---|---|---|---|
| | | 9:1 | 7:1 | 5:1 | intensity |
| 1 | 2 | 3 | 4 | 5 | 6 |
| 1 | Patient B. | + | − | − | weak |
| 2 | Patient L. | + | − | − | weak |
| 3 | Patient Ya. | + | − | − | weak |
| 4 | Patient Sh. | +++ | ++ | − | moderate |
| 5 | Patient M. | +++ | ++ | − | moderate |
| 6 | Patient R. | +++ | ++ | − | moderate |
| 7 | Patient O. | +++ | ++ | − | moderate |
| 8 | Patient K. | +++ | ++ | − | moderate |
| 9 | Patient S. | +++ | ++ | − | moderate |
| 10 | Patient U. | +++ | ++ | − | moderate |
| 11 | Patient A. | +++ | +++ | +++ | well pronounced |
| 12 | Patient D. | +++ | +++ | +++ | well pronounced |

| Nos. | Patients | Time (months) of detection of calculus during subsequent clinical examinations |
|---|---|---|
| 1 | 2 | 7 |
| 1 | Patient B. | 27 months |
| 2 | Patient L. | 24 |
| 3 | Patient Ya. | 29 |
| 4 | Patient Sh. | 7 |
| 5 | Patient M. | 8 |
| 6 | Patient R. | 8 |
| 7 | Patient O. | 7 months |
| 8 | Patient K. | 9 |
| 9 | Patient S. | 8 |
| 10 | Patient U. | 7 |
| 11 | Patient A. | 3 |
| 12 | Patient D. | 2 |

Notes:
(+) - the presence of separate, singly occuring crystals in the marginal zone of a urine sample.
(++) - conglamerates of crystals.
(+++) - complete crystallization of the marginal zone.

TABLE 2

The results of clinical and laboratory tests on practically healthy persons in their preclinical urolithiasis stage

| Nos. | Number of persons under examination | Urine/aqueous albumin solution ratio 9:1 | 7:1 | 5:1 | Extent of lithogenesis process intensity | Time of detection of a calculus during next clinical tests (months) |
|---|---|---|---|---|---|---|
| 1 | 61 | + | − | − | weak | 24–30 |
| 2 | 49 | +++ | ++ | − | moderate | 7–8 |
| 3 | 18 | +++ | +++ | +++ | well pronounced | 2–3 |

Notes:
(+) - the presence of separate, singly occuring crystals in the marginal zone of a urine sample.
(++) - conglomerates of crystals.
(+++) - complete crystallization of the marginal zone.

As seen from the results reported in Tables 1 and 2, there is a 100%-agreement between the laboratory and clinical test results indicative of the formation of a urate calculus. In one group of "calculi discharger" patients affected by a lithogenesis process with a deeply pronounced intensity (i.e. a group in which a complete crystallization of the marginal zone was observed), newly formed calculi were detected upon expiration of some 2–3 months; in another groups of patients (those with a partial crystallization of the crystalline conglomerates in the marginal zone) affected by a lithogenesis process with a moderate intensity extent, newly formed calculi were detected upon expiration of some 7–8 months; and in third group of patients affected with a weakly pronounced lithogenesis process (i.e. separate, singly occurring crystals in the marginal zone), newly formed calculi were found upon expiration of 2–2.5 years. The same is valid for the results of clinical and laboratory tests on practically healthy persons affected by urolithiasis in its pre-clinical stage (Table 2). Consequently, the method in accordance with the present invention makes it possible to draw a conclusion on the lithogenesis process intensity (i.e. to assess the extent of the process intensity) and to make judgement on the time it takes to form a calculus.

Simultaneously with evaluation of the extent of the lithogenesis process intensity, studies of the composition of calculi-forming urate salts were conducted in 13 patients affected with urolithiasis (with a definitely established extent of the lithogenesis process). Out of these 13 patients 6 patients belonged to the category of "calculi dischargers", and 7 underwent lithotripsy. A urine sample was applied onto a mecroscopic slide to dry up. A complete crystallization of the marginal zone was observed (which bespoke of a deeply pronounced lithogenes is process). The phase or elemental composition of these crystalline formations was determined by the X-ray structure analysis and X-ray spectrum microanalysis. The results of these analyses of the elemental (phase) composition of crystalline formations occurring in the marginal zone of urine samples were compared with the results obtained by analyzing the urate calculi actually released later.

As follows from the analytical results reported in Table 3, the results of an analysis of the composition of crystalline formations of the marginal zone of

TABLE 3

Comparative results of the analyses of salt constitutions of crystalline formations occurring in the marginal zone of urine samples and of actually discharged urate calculi

| Nos. 1 | Patients 2 | Diagnosis 3 | Elemental (phase) constitution of salts in crystalline formations in marginal zone of a urine sample 4 |
|---|---|---|---|
| 1 | Patient K. | Urolithiasis | Uric acid* |
| 2 | Patient P. | Urolithiasis | Uric acid. Acid urate of ammonium* |
| 3 | Patient H. | Urolithiasis | Uric acid. Acid urate of ammonium* |
| 4 | Patient L. | Urolithiasis | Uric acid* |
| 5 | Patient R. | Urolithiasis. Secondary pyelonephritis | Calcium, phosphorus, magnesium** |
| 6 | Patient A. | Urolithiasis. Secondary pyelonephritis | Calcium, phosphorus, magnesium |
| 7 | Patient N. | Urolithiasis. Secondary pyelonephritis | Phosphorus, calcium, zinc** |
| 8 | Patient V. | Urolithiasis. Secondary pyelonephritis | Phosphorus, calcium** |
| 9 | Patient A. | Urolithiasis | Phosphorus, calcium, magnesium** |
| 10 | Patient I. | " | Phosphorus, calcium** |
| 11 | Patient G. | Urolithiasis. Secondary pyelonephritis | Calcium** |
| 12 | Patient T. | Urolithiasis. Secondary pyelonephritis | Calcium** |
| 13 | Patient A. | Urolithiasis. Secondary pyelonephritis | Calcium** |

| Nos. 1 | Patients 2 | Composition of discharged urate calculi (prevailing in surface layer of a calculus) 5 |
|---|---|---|
| 1 | Patient K. | Urates |
| 2 | Patient P. | Urates |
| 3 | Patient H. | Urates |
| 4 | Patient L. | Urates |
| 5 | Patient R. | Phosphates |
| 6 | Patient A. | Phosphates |
| 7 | Patient N. | Phosphates |
| 8 | Patient V. | Phosphates |
| 9 | Patient A. | Phosphates |
| 10 | Patient I. | Phosphates |
| 11 | Patient G. | Oxalates |
| 12 | Patient T. | Oxalates |
| 13 | Patient A. | Oxalates |

*the results of an X-ray structure analysis.
**the results of an X-ray spectrum microanalysis.

a urine sample are matched by the results of a study of the composition of an actually discharged urate calculus.

Consequently, the method of the present invention makes it possible to predict or to determine the salt constitution of a calculus at the pre-clinical stages of development of urolithiasis, and this fact may be advantageously used for prevention of the concrement formation.

For better understanding of the essence of the present invention, the following specific embodiments of the present method are reported:

EXAMPLE 1

Patient B., 50 years old, was taken under observation by a clinical laboratory for 2 years. After discharge of a calculus from his body, he was taken under dynamic observation. His urine was investigated weekly by the present method. The following procedure was used for investigations:

An aqueous albumin solution was added to his urine sample in a ratio of 9:1, 7:1 or 5:1, respectively. The resultant mixture was applied drop-wise onto a microscopic slide and dried up at room temperature for 24 hours. The nature of salts crystallized in the marginal zone of the urine sample was next determined. During four months, there was observed a deeply pronounced extent of the calculus formation process intensity (i.e. a complete crystallization of the marginal zone of the urine sample was observed). Simultaneously, by means of an X-ray spectrum microanalysis, the elemental constitution of crystalline formations in the marginal zone was established. For a comparative analysis, the elemental constitution of the central zone of the same urine sample was determined. There was established that a considerable excess in the contents of some individual elements in the marginal zone over those in the central zone becomes the basis for calculi-forming salts.

The results of determination of the composition of calculi-forming salts are confirmed by the results of a calculus composition analysis after the calculus discharge from the body. The results of a study are reported in Table 4 below:

TABLE 4

The results of a comparative analysis of the elemental constitutions of the central and marginal zone of a urine sample and a discharged urate calculus

| Material under study | Elements, %% | | | | |
|---|---|---|---|---|---|
| | Na | Mg | P | S | Cl |
| 1 | 2 | 3 | 4 | 5 | 6 |
| 1. Urine sample (central zone) | 27.4 | 1.1 | 3.4 | 1.1 | 62.6 |
| 2. Urine sample (marginal zone) | 17.3 | 0.9 | 14.6 | 9.5 | 39.6 |
| 3. Extracted urate calculus | — | 3.3 | 30.3 | — | — |

| Material under study | Elements, %% | | | |
|---|---|---|---|---|
| | K | Ca | Zn | Si |
| 1 | 7 | 8 | 9 | 10 |
| 1. Urine sample (central zone) | 3.3 | — | — | — |
| 2. Urine sample (marginal zone) | 11.6 | 6.1 | — | — |
| 3. Extracted urate calculus | — | 64.2 | — | — |

As follows from Table 4, calcium and phosphorus are the main constituents of calculi-forming salts, and this inference is confirmed by the constitution of the calculus after its extraction from the patient's body.

After removal of the calculus from the body, a medical treatment course was prescribed to the patient and his urine was examined weekly for two more years. The results of dynamic observation (i.e. the results of periodically evaluating the extent of the lighogenesis process intensity) of the patient in question are reported in Table 5 below:

TABLE 5

The results of observing the extent of the lithogenesis process intensity in patient B. as viewed dynamically from the very beginning of the treatment course

| Examination periodicity | Crystallization degree of the marginal zone of a urine sample at a urine/aqueous albumin solution ratio of | | | Extent of the lithogenesis process intensity |
|---|---|---|---|---|
| | 9:1 | 7:1 | 5:1 | |
| 1 | 2 | 3 | 4 | 5 |
| 1 week | ++ | ++ | − | moderate |
| 1 month | + | + | − | weak |
| 2–4 months | − | − | − | no process |
| 5–7 months | ++ | + | − | moderate |
| 8 months | + | − | − | weak |
| 9–13 months | − | − | − | no process |
| 14 months | + | − | − | weak |
| 15–20 months | + | − | − | weak |

Note:
+ the presence of separate, singly occurring crystals.
++ conglomerates of crystals.
− no crystals are observed.

EXAMPLE 2

The extent of the lithogenesis process intensity in a urine sample of the patient H. was evaluated using the procedure described in Example 1. It was established that the patient H. was affected with a deeply pronounced lithogenesis intensity (i.e. a complete crystallization of the marginal zone of the urine sample was observed). By means of an X-ray spectrum microanalysis, the elemental constitution of crystalline formations in the marginal zone was determined. For the sake of comparison, a comparative analysis was conducted of the elemental constitutions of the marginal and central zones of a dried urine sample. The results thus-obtained of determining the constitution of lithogenic salts were confirmed by an analysis of the composition of the urate calculus after its extraction from the patient's body. The analytical results are reported in Table 6.

As seen from the data of Table 6, it is mainly calcium that is the main calculus-forming element, and this conclusion is confirmed by the fact that the calcium content in the calculus is 93%.

TABLE 6

The results of a comparative analysis of the elemental constitutions of the central and marginal zones of a urine sample and of an extracted urate calculus

| Material under study | Elements, %% | | | | |
|---|---|---|---|---|---|
| | Na | Mg | P | S | Cl |
| 1 | 2 | 3 | 4 | 5 | 6 |
| 1. Urine sample (central zone) | 26.2 | 2.0 | 15.1 | 8.9 | 30.5 |
| 2. Urine sample (marginal zone) | 27.6 | 2.1 | 19.6 | 12.3 | 26.0 |
| 3. Extracted urate calculus | 1.5 | — | 4.1 | 0.5 | — |

TABLE 6-continued

The results of a comparative analysis of the elemental constitutions of the central and marginal zones of a urine sample and of an extracted urate calculus

| Material under study | Elements, %% | | | |
|---|---|---|---|---|
| 1 | K 7 | Ca 8 | Zn 9 | Si 10 |
| 1. Urine sample (central zone) | 13.0 | 2.6 | — | — |
| 2. Urine sample (marginal zone) | 4.8 | 7.6 | — | — |
| 3. Extracted urate calculus | — | 93.0 | — | — |

EXAMPLE 3

The extent of the lithogenesis process intensity in a urine sample of the patient K. was evaluated using the procedure described in Example 1. It was established that the patient K. was affected with a deeply pronounced lithogenesis intensity (i.e. a complete crystallization of the marginal zone in his urine sample was observed). By means of an X-ray spectrum microanalysis, the elemental constitution of crystalline formations in the marginal zone was determined. A comparative analysis was conducted of the elemental constitutions of the marginal and central zones of a dried urine sample. The results of determination of the composition if calculi-forming salts were confirmed by the actual composition of a calculus after its extraction from the patient's body. The analytical results are reported in Table 7 below:

TABLE 7

The results of a comparative analysis of the elemental constitutions of the central and marginal zones of a urine sample and of an extracted urate calculus

| Material under study | Elements, %% | | | | |
|---|---|---|---|---|---|
| 1 | Na 2 | Mg 3 | P 4 | S 5 | Cl 6 |
| 1. Urine sample (central zone) | 17.2 | — | 15.8 | 12.2 | 31.1 |
| 2. Urine sample (marginal zone) | 12.7 | 3.9 | 23.3 | 9.2 | 22.4 |
| 3. Extracted urate calculas | — | 14.0 | 39.3 | — | — |

| Material under study | Elements, %% | | | |
|---|---|---|---|---|
| 1 | K 7 | Ca 8 | Zn 9 | Si 10 |
| 1. Urine sample (central zone) | 19.7 | 2.6 | — | — |
| 2. Urine sample (marginal zone) | 12.5 | 5.5 | — | — |
| 3. Retracted urate calculus | — | 44.7 | — | — |

As follows from Table 7, calcium, phosphorus and magnesium are the main constituents of calculi-forming salts, and this conclusion is confirmed by the actual composition of the calculus after its extraction: Ca 44.7%, P 39.3%, Mg 14.0%.

EXAMPLE 4

The extent of the lithogenesis process intensity in a urine sample taken from the patient S. was evaluated using the procedure described in Example 1. It was established that the patient S. was affected with a highly intensive lithogenesis process (i.e. a complete crystallization of the marginal zone in his urine sample was observed). By means of an X-ray spectrum microanalysis, the elemental constitution of crystalline formations in the marginal zone was determined. A comparative analysis was conducted of the elemental constitutions of the marginal and central zones of a dried urine sample. After establishing the fact that the patient S. was affected with a highly intensive lithogenesis process and determining the composition of the calculi-forming salts, the patient S. underwent an individual therapy course. His urine sample was again subjected to an analysis. The result thus-obtained are reported in Table 8 below:

TABLE 8

The results of a comparative analysis of the elemental constitutions of the central and marginal zones of a urine sample and of an extracted urate calculus (%%)

| Examination period 1 | Lithogenesis intensity extent 2 | Material under study 3 | Elements, %% | | |
|---|---|---|---|---|---|
| | | | Na 4 | Mg 5 | P 6 |
| Before treatment | Highly pronounced | Urine sample (centr. zone) | 25.2 | 1.5 | 7.1 |
| | | (marg. zone) | 14.1 | 0.2 | 14.6 |
| After treatment | No process | (central zone) | 33.4 | 1.0 | 10.6 |
| | | (marg. zone) | 34.6 | — | 10.6 |

| Examination period 1 | Lithogenesis intensity extent 2 | Material under study 3 | Elements, %% | | |
|---|---|---|---|---|---|
| | | | S 7 | Cl 8 | K 9 |
| Before treatment | Highly pronounced | Urine sample (central zone) | 7.8 | 37.1 | 16.4 |
| | | (marg. zone) | 2.7 | 17.0 | 8.4 |
| After treatment | No process | (central zone) | 10.1 | 35.9 | 7.1 |
| | | (marg. zone) | 8.3 | 35.9 | 6.4 |

| Examination period 1 | Lithogenesis intensity extent 2 | Material under study 3 | Elements, %% | | |
|---|---|---|---|---|---|
| | | | Ca 10 | Zn 11 | Si 12 |
| Before treatment | Highly pronounced | Urine sample (central zone) | 1.7 | 0.2 | — |
| | | (marg. zone) | 4.7 | 0.2 | — |
| After treatment | No process | (central zone) | 1.4 | 1.3 | — |
| | | (marg. zone) | 0.4 | 1.1 | — |

As follows from Table 8, calcium and phosphorus were the main constituents of calculi-forming salts (before treatment), whereas after treatment the lithogenesis process was altogether discontinued.

Industrial Applicability

The method of the present invention may be applicable in clinical and scientific laboratory research for analysis of the extent of lithogenesis process intensity, for carrying out studies of the dynamic aspects of lithogenesis processes, for determining the salt composition of calculi at early urolithiasis stages, for preventing urate calculi formation and for prescribing an individual therapy course in urolithiasis cases.

What is claimed is:

1. A method of determining the severity of a lithogenesis condition and a composition of calculi forming salts in a urine sample comprising mixing a urine sample with an aqueous protein solution to form a mixture having a urine to protein solution ratio of 9:1, 7:1 or 5:1, applying a drop of said mixture to a smooth surface, drying the drop for at least 24 hours, determining the extent of salt crystallization in a peripheral zone of the dried sample mixture, classifying the presence of singly occurring crystals, crystal conglomerates or complete crystallization respectfully as indicative of a weak, moderate or severe lithogenesis condition, determining a salt composition for the crystals in the peripheral zone and a central zone of the dried sample and determining the composition of the calculi forming salts in the urine sample through a comparative analysis of the salt compositions of the two zones of the dried sample mixture.

2. A method as claimed in claim 1 wherein said aqueous protein solution is an 8–12% aqueous albumin solution.

3. A method as claimed in claim 2 wherein X-ray spectrum microanalysis is used to determine the crystalline formations.

4. A method as claimed in claim 1 wherein the drying of said drop of the mixture produced by mixing a urine sample with an aqueous protein solution is carried out at room temperature.

5. A method as claimed in claim 4 wherein X-ray spectrum microanalysis is used to determine the composition of crystalline formations.

6. A method as claimed in claim 1 wherein X-ray spectrum microanalysis is used to determine the composition of crystalline formations.

7. A method of determining the severity of a lithogenesis condition and a composition of calculi forming salts in a urine sample comprising mixing a urine sample with an aqueous protein solution to form mixtures having a urine to protein solution ratio of 9:1, 7:1 and 5:1, applying a drop of each mixture to a smooth surface, drying the drops for at least 24 hours, determining the extent of salt crystallization in a peripheral zone of the dried sample mixtures, classifying the presence of singly occurring crystals, crystal conglomerates or complete crystallization respectfully as indicative of a weak, moderate or severe lithogenesis condition, determining a salt composition for the crystals in the peripheral zone and a central zone of the dried sample mixtures and determining the compositions of the calculi forming salts in the urine sample through a comparative analysis of the salt compositions of the two zones of the dried sample mixtures.

8. A method as claimed in claim 7 wherein said aqueous protein solution is an 8–12% aqueous albumin solution.

9. A method as claimed in claim 8 wherein the X-ray spectrum microanalysis is used to determine the composition of crystalline formations.

10. A method as claimed in claim 7 wherein the drying of said drops of the mixtures produced by mixing a urine sample with an aqueous protein solution is carried out at room temperature.

11. A method as claimed in claim 10 wherein the X-ray spectrum microanalysis is used to determine the composition of crystalline formations.

12. A method as claimed in claim 7 wherein X-ray spectrum microanalysis is used to determine the composition of crystalline formations.

13. A method of determining the severity of a lithogenesis condition and a composition of calculi forming salts in a urine sample comprising mixing a urine sample with an aqueous protein solution to form at least two mixtures; each of said mixtures having a urine to protein solution ratio of 9:1, 7:1 or 5:1 the ratio of urine to protein solution in each of said mixtures being different; applying a drop of each mixture to a smooth surface, drying the drops for at least 24 hours, determining the extent of salt crystallization in a peripheral zone of the dried sample mixtures, classifying the presence of singly occurring crystals, crystal conglomerates or complete crystallization respectfully as indicative of a weak, moderate or severe lithogenesis condition, determining a salt composition for the crystals in the peripheral zone and a central zone of the dried sample mixtures and determining the compositions of the calculi forming salts in the urine sample through a comparative analysis of the salt compositions of the two zones of the dried sample mixtures.

14. A method as claimed in claim 13 wherein said aqueous protein solution is an 8–12% aqueous albumin solution.

15. A method as claimed in claim 14 wherein the X-ray spectrum microanalysis is used to determine the composition of crystalline formations.

16. A method as claimed in claim 13 wherein the drying of said drops of the mixtures produced by mixing a urine sample with an aqueous protein solution is carried out at room temperature.

17. A method as claimed in claim 16 wherein the X-ray spectrum microanalysis is used to determine the composition of crystalline formations.

18. A method as claimed in claim 13 wherein X-ray spectrum microanalysis is used to determine the composition of crystalline formations.

* * * * *